United States Patent
Müller

(10) Patent No.: US 12,201,273 B2
(45) Date of Patent: Jan. 21, 2025

(54) METHOD AND DEVICE FOR VIDEO ENDOSCOPY WITH FLUORESCENT LIGHT

(71) Applicant: Xion GmbH, Berlin (DE)

(72) Inventor: Holger Müller, Glienicke-Nordbahn (DE)

(73) Assignee: XION GMBH, Berlin (DE)

( * ) Notice: Subject to any disclaimer, the term of this patent is extended or adjusted under 35 U.S.C. 154(b) by 76 days.

(21) Appl. No.: 17/946,573

(22) Filed: Sep. 16, 2022

(65) Prior Publication Data

US 2023/0083555 A1 Mar. 16, 2023

(30) Foreign Application Priority Data

Sep. 16, 2021 (DE) .......................... 102021124010.7

(51) Int. Cl.
*A61B 1/06* (2006.01)
*A61B 1/00* (2006.01)
(Continued)

(52) U.S. Cl.
CPC ........ *A61B 1/0661* (2013.01); *A61B 1/00006* (2013.01); *A61B 1/000095* (2022.02);
(Continued)

(58) Field of Classification Search
CPC .............. A61B 1/0661; A61B 1/00006; A61B 1/000095; A61B 1/0005; A61B 1/043;
(Continued)

(56) References Cited

U.S. PATENT DOCUMENTS

| 4,821,117 A | 4/1989 | Sekiguchi |
| 8,428,318 B2 | 4/2013 | Zhuo et al. |

(Continued)

FOREIGN PATENT DOCUMENTS

| DE | 19835067 A1 | 2/2000 |
| DE | 102016217792 A1 | 3/2018 |

(Continued)

OTHER PUBLICATIONS

German Search Report and Opinion dated May 2, 2022 issued by the GPTO in corresponding Application No. DE102021124010.7, 13 pages.

*Primary Examiner* — Jared Walker
(74) *Attorney, Agent, or Firm* — Ware, Fressola, Maguire & Barber LLP

(57) ABSTRACT

The invention relates to a method for performing video endoscopy with fluorescent light, comprising capturing a first image sequence comprised of temporally consecutive single images, using an endoscopic video system, capturing a second image sequence comprised of temporally consecutive fluorescent images, using the same endoscopic video system, forming a transformation function between different single images of the first image sequence, applying the transformation function to the consecutive fluorescent images of the second image sequence associated with the single images of the first image sequence to obtain transformed fluorescent images, superimposing a current fluorescent image of the second image sequence with at least one or several transformed fluorescent images obtained from the fluorescent images immediately preceding the current fluorescent image in the second image sequence to obtain an improved fluorescent image, and displaying a respective fluorescent image resulting in an improved second image sequence that is comprised of improved fluorescent images.

17 Claims, 14 Drawing Sheets

(51) Int. Cl.
  *A61B 1/04*   (2006.01)
  *G01N 21/64*  (2006.01)
  *G02B 23/24*  (2006.01)
  *H04N 23/50*  (2023.01)

(52) U.S. Cl.
  CPC ............ *A61B 1/0005* (2013.01); *A61B 1/043* (2013.01); *A61B 1/0655* (2022.02); *G01N 21/6456* (2013.01); *G02B 23/2461* (2013.01); *G02B 2207/113* (2013.01); *H04N 23/555* (2023.01)

(58) Field of Classification Search
  CPC ............ A61B 1/0655; A61B 1/00009; G01N 21/6456; G02B 23/2461; G02B 2207/113; H04N 23/555
  See application file for complete search history.

(56) References Cited

U.S. PATENT DOCUMENTS

| | | | |
|---|---|---|---|
| 8,721,532 | B2 | 5/2014 | Takei et al. |
| 2004/0210107 | A1 | 10/2004 | Tani et al. |
| 2014/0081083 | A1* | 3/2014 | Morita ............... A61B 1/00177 600/109 |
| 2017/0354392 | A1 | 12/2017 | Fengler et al. |
| 2018/0220052 | A1* | 8/2018 | Granneman ........... H04N 23/73 |
| 2020/0043160 | A1* | 2/2020 | Mizukura ............. G06T 7/0012 |
| 2020/0397253 | A1* | 12/2020 | Talbert .................. A61B 1/043 |

FOREIGN PATENT DOCUMENTS

| | | |
|---|---|---|
| DE | 112016004455 T5 | 8/2018 |
| EP | 2209303 A2 | 7/2010 |
| JP | 2012-050617 A | 3/2012 |
| JP | 2012-085916 A | 5/2012 |

* cited by examiner

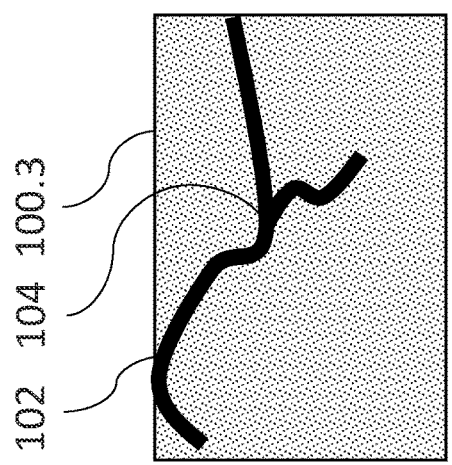 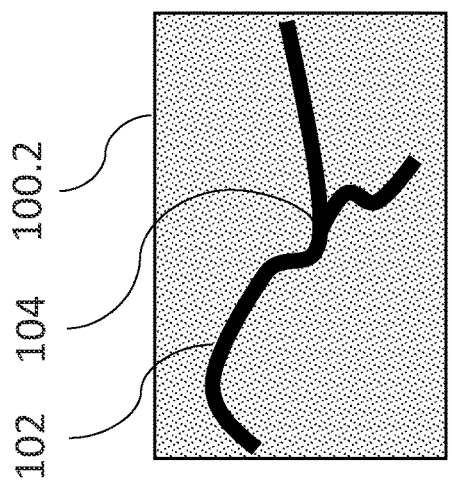 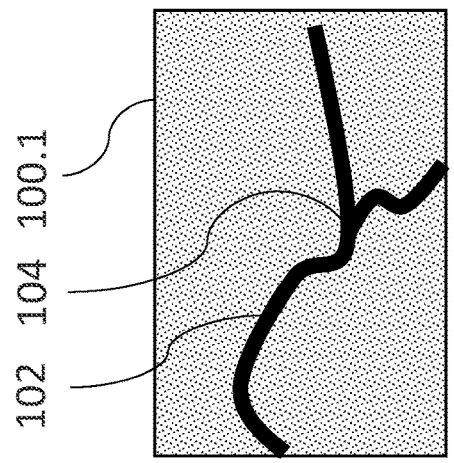
Fig. 2A
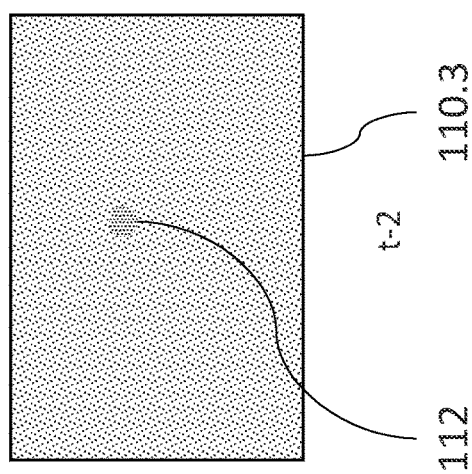 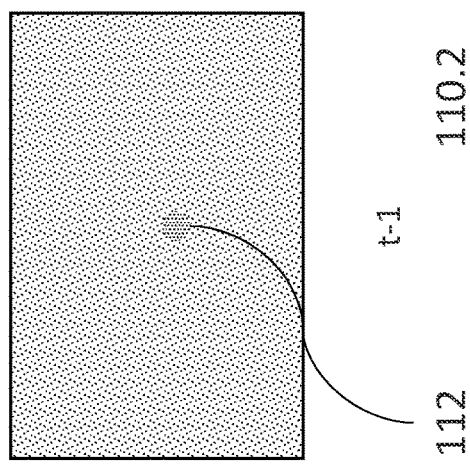 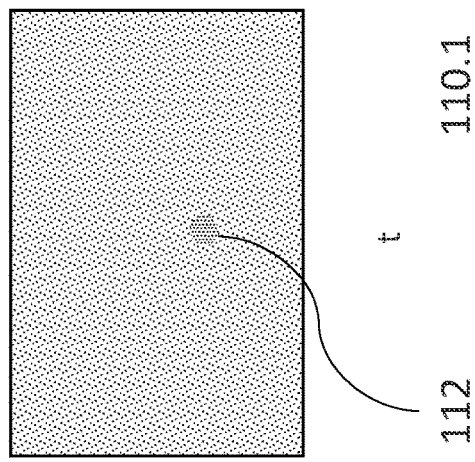
Fig. 2B

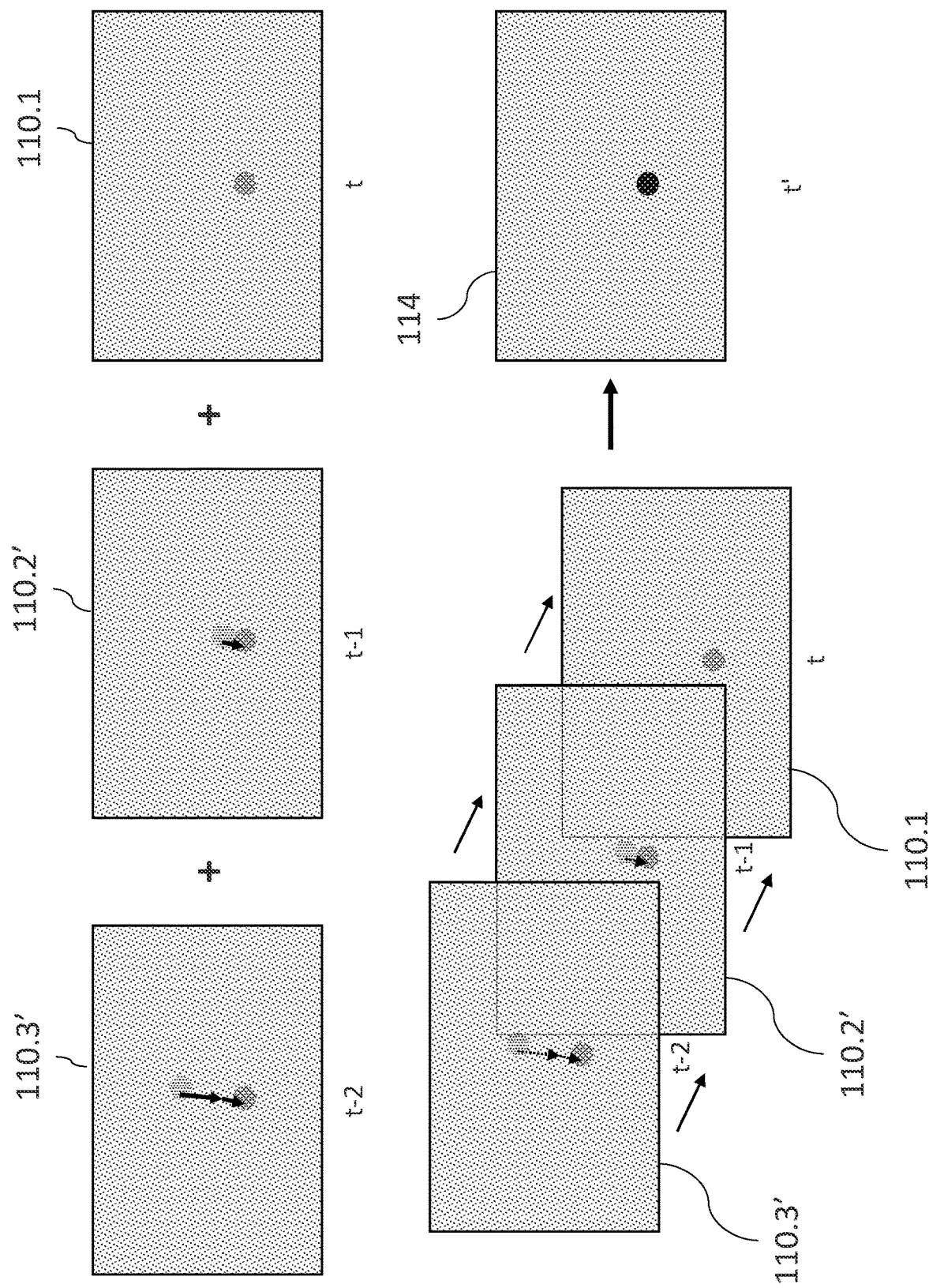

METHOD AND DEVICE FOR VIDEO ENDOSCOPY WITH FLUORESCENT LIGHT

CROSS-REFERENCE TO RELATED APPLICATION

This application claims priority under 35 USC § 119 to German Patent Application No. 102021124010.7 filed on Sep. 16, 2021, which is hereby incorporated by reference in its entirety.

TECHNICAL FIELD

The invention relates to a method and an apparatus for video endoscopy with fluorescent light. A device for video endoscopy is also understood to be a camera head with interchangeably connected endoscopes and thus not only—but also—a video endoscope in the narrower sense. In most cases, a video endoscope in the narrower sense is understood to be an endoscope with a permanently installed camera.

BACKGROUND OF THE INVENTION

Video systems for endoscopic display of fluorescent images are well known. They are often used in surgical procedures. For example, tissue affected by cancer can be stained using a fluorescent dye. The fluorescent glow makes it easier for the surgeon to distinguish the affected tissue from healthy tissue, thus making it safer to surgically remove it.

Endoscopic video systems for capturing fluorescent images can typically also capture images under visible light. To this end, an object is illuminated with visible light, and the visible light reflected by the object is recorded. An image sequence of single images recorded in this manner then results in a video sequence that shows the appearance of the object under visible light. In addition, an object can be irradiated simultaneously or alternately with fluorescence-stimulating radiation in order to capture a second image sequence with fluorescent images. Single images that are captured under visible light and make up the first image sequence will, in the following, be referred to simply as single images (in the narrower sense) or as reflection images, while single images of the second image sequence captured under fluorescence-stimulating radiation will be referred to as fluorescent images.

The single images and fluorescent images of both image sequences can be captured simultaneously if the wavelengths of the fluorescence and/or of the fluorescence-stimulating radiation are different than the wavelength of the visible light used for the reflection images A fluorescence channel and a reflection channel (i.e. the channel for reflected light) can thus be separated by means of optical filters, even if both channels are made up of simultaneously captured single or fluorescent images of the associated first and second image sequence.

It is also possible to alternate between capturing one single image or several single images under visible light and one fluorescent image or several fluorescent images, with the time delay between the single image and the associated fluorescent image being very small. The fluorescence channel and the reflection channel are thus temporally separated because the single images or the fluorescent images of the associated first and second image sequence are temporally offset from each other.

In both cases, an optical blocking filter is usually used in addition in front of the camera to block the stimulating light reflected by the object, because this reflected stimulating light would otherwise outshine the light emitted by fluorescence.

As a general rule, the luminance of a fluorescent image in endoscopy is very low. This is why a strong signal amplification is needed when using highly sensitive image sensors in order to display the fluorescent glow. US 2004/0210107 A1 and U.S. Pat. No. 8,721,532 B2 therefore recommend adding adjacent pixels of the fluorescent image for signal amplification. While the addition does increase the luminance of large fluorescent surfaces, it also decreases the optical resolution of the fluorescent image. As a result, fine object structures are difficult to detect when using this method.

In U.S. Pat. No. 8,428,318 B2, in a video sequence of fluorescent images, a noise filter and a convolution filter are used for the images. The images are then motion-corrected by means of affine transformation, and an averaging of the images is performed for further noise reduction. Due to the low pass effect of the filters, this method is only suitable for improving the rendering of coarse structures that fluoresce over a large area. In addition, due to the strong image noise of the fluorescent image, calculation of the affine transformation is only possible if the image has highly fluorescing structures.

U.S. Pat. No. 4,821,117 A suggests amplification of the fluorescent image by means of an image intensifier. The disadvantage there is the high degree of technical complexity because of the image intensifier. In addition, image intensifiers usually only have a low resolution, which is why this set-up does not improve the rendering of fine structures with low fluorescence.

SUMMARY OF THE INVENTION

It is the object of the invention to create a method and an apparatus for enabling improved video endoscopy with fluorescent light.

According to the invention, a method comprising the following steps is provided for this purpose:

Capturing a first image sequence (first video sequence), which is comprised of temporally consecutive single images, using an endoscopic video system in which an object is illuminated and the light reflected by the object is captured as a single image;

Capturing a second image sequence (second video sequence), which is comprised of temporally consecutive fluorescent images, using the same endoscopic video system in which the object is irradiated with fluorescence-stimulating radiation and the light emitted by the object is captured as a fluorescent image, wherein the capturing of the first and second image sequence—and thus of the single images and the fluorescent images—occurs either simultaneously, or a single image or several single images and a fluorescent image or several fluorescent images are captured alternately so that each single image can be associated with a fluorescent image captured immediately before or immediately after—and thus at least approximately at the same time;

Determining a transformation function—in the simplest case a linear displacement—between consecutive single images;

Applying the transformation function to the consecutive fluorescent images associated with the single images to obtain transformed fluorescent images;

Superimposing a current fluorescent image of the second image sequence with at least one or several transformed fluorescent images obtained from the current fluorescent image in the fluorescent images prior to the second image sequence to obtain an improved fluorescent image; and Displaying a respective fluorescent image improved in this manner, resulting in an improved second image sequence that is comprised of improved fluorescent images.

The first sequence of images is comprised of single images, i.e. each single image of the first image sequence is a frame of a first video sequence. Likewise, the second sequence of fluorescent images is comprised of fluorescent images, i.e. each fluorescent image of the second image sequence is a frame of a second video sequence. The individual (i.e. single) images of the first image sequence are also called "reflection" images because result from capturing reflected light while the individual images of the second images are fluorescent images because they show the captured fluorescence.

According to the method a video endoscope is initially used to capture two video sequences simultaneously or quasi simultaneously. A first video sequence is created from a first image sequence that is comprised of individual images captured of an object using the light reflected by this object. At the same time—either precisely simultaneously or alternately with the individual images of the first image sequence—images of the object are captured while the object is illuminated with fluorescence-stimulating radiation in order to create a second video sequence that is made up of a second image sequence comprised of fluorescent images. The term fluorescent images is used here for the individual images captured of an object using the light the object emits by fluorescence.

Due to the fact that the single images of the first image sequence (and thus of the first video sequence) are captured simultaneously or alternately with the fluorescent images of the second image sequence (and thus of the second video sequence), either a simultaneously captured single image of the first image sequence can be associated with each fluorescent image or—if the single images and fluorescent images are captured alternately—at least an immediately preceding or subsequent single image can be associated with each fluorescent image. Since the ratio of the number of single images and fluorescent images does not necessarily have to be one-to-one, but two reflection images and one fluorescent image—or vice versa—can respectively be captured in a recurring cycle, for example, one fluorescent image can also be associated with two single images—or vice versa, one single image with two fluorescent images.

Since the single images and the fluorescent images are captured simultaneously or quasi simultaneously using the same video endoscope, single and fluorescent images associated with each other respectively show the same or approximately the same scene from the same or approximately the same perspective. This is also true if the endoscope is moved or the object moves, for example. In both cases, consecutive single images of the first image sequence will differ due to the movement of the endoscope or the object. Consecutive fluorescent images of the second image sequence to be associated with the single images will differ in the same way or approximately the same way. The differences between two consecutive single images may be simply that the depictions of the object in the two single images are displaced and/or distorted relative to one another. Due to distortions of the endoscope optics—for example barrel distortion—or a movement of the object that is only reflected in one part of the captured image, it is also possible that two consecutive single images differ not simply because of linear displacements or distortions. Rather, the differences between two consecutive single images have to be described by means of a more complex transformation function that maps the different displacements, distortions, stretches or compressions of the various areas of the single image. In each of these cases it is possible, using means known per se, to identify the transformation function that can be used to transfer a single image of the first image sequence into a preceding or subsequent single image of the first image sequence.

The invention is based on the concept that the image features used for identifying the transformation function can be identified better and more precisely in the single images (i.e. the reflection images) of the first image sequence since the single images of the first image sequence, even with low depth of field, usually show sufficient image or object features that are clearly identifiable. It is thus possible to determine, from the single images of the first image sequence, transformation functions that describe how—i.e. by using which transformation function—a single image of the first image sequence can be mapped to another single image of the same image sequence so that image and object features are in the same place.

The transformation functions thus determined can be applied to consecutive fluorescent images of the second image sequence. This is particularly easy if the reflection images and the fluorescent images were captured simultaneously. If reflection images and fluorescent images are captured sequentially in time—i.e. alternately or cyclically, for example—a temporal interpolation may be required in order to calculate a transformation suitable for the time of recording of the fluorescent image. In any case, the requirement of detecting objects in the fluorescent image is avoided with the method according to the invention.

Accordingly, the method comprises determining the transformation functions between consecutive single images on the basis of the single images of the first image sequence, and applying these transformation functions to the respective fluorescent images of the second image sequence. This way, it is possible to create the direct transformation to the respective last image and thus also the corresponding transformation function, for example. The application of the transformation function can comprise interpolation if the single images and fluorescent images are captured alternately or cyclically—and thus with a time delay. One or several position-enhanced, transformed fluorescent images are obtained in this way, which can then be superimposed, resulting in a fluorescent image that has been improved with regard to the signal-to-noise ratio.

Correspondingly, each fluorescent image of the second image sequence can be superimposed with one, two or several transformed preceding fluorescent images and thus improved, resulting in an improved second image sequence that is comprised of improved fluorescent images. This way, an improved video sequence with fluorescent images is obtained using the method.

According to a further aspect, an apparatus is proposed that comprises a video endoscopy system with an image processing device. The video endoscopy system is configured to capture two image sequences, namely a first image sequence comprised of temporally consecutive single images, with an object being illuminated and the light reflected by the object being captured as a single image, and a second image sequence comprised of temporally consecutive fluorescent images, with the object being irradiated with fluorescence-stimulating radiation and the light emitted by the object being captured as a fluorescent image. The image processing device is configured to p1 associate one or several single images of the first image sequence with one or several fluorescent images of the second image sequence that were captured at least approximately simultaneously;

derive transformation functions from the single images of the first image sequence, which transformation functions describe the geometric change of image features between two single images;

apply the derived transformation functions to the fluorescent images that correspond to the single images; and superimpose the fluorescent images transformed this way into an improved fluorescent image.

According to one variant, the video endoscopy system is configured to capture two image sequences in such a way that capturing of the single images and of the fluorescent images of the first or second image sequence occurs simultaneously so that each single image can be associated with a simultaneously captured fluorescent image.

According to a second variant, the video endoscopy system is configured to capture two image sequences in such a way that a single image or several single images and a fluorescent image or several fluorescent images are captured alternately, so that each single image can be associated with a fluorescent image that was captured before or after the single image with minimal temporal offset.

The invention takes into account that, in video endoscopy, the fluorescent light captured by the image sensor is generally very weak. This is why it is particularly difficult to display weakly fluorescing objects. The weak fluorescence is close to the detection threshold and hardly distinguishable from the image noise of the image sensors light receiver. Increasing the exposure time, which is common practice especially in astronomy, is not practical for surgical endoscopy because an endoscopic video system is supposed to smoothly reproduce movements of objects in the image at a high frame rate. This is the only way optimal handling of the endoscope and of the surgical instruments is possible based on the real-time image on the monitor.

While known methods and devices can improve the reproduction of weak fluorescence, the optical image resolution will be unintentionally decreased by improving the light sensitivity. Consequently, a good identification of weakly fluorescing structures is limited to larger structures with sufficient expansion of fluorescence. Smaller structures are only reproduced if they are brightly fluorescent. However, fine structures that are of diagnostic interest are often only weakly fluorescent because of their small dimensions.

As a result, such fine and weakly fluorescing structures cannot be reproduced when using the known methods and endoscopic video systems.

In practice, endoscopes are frequently used for displaying and capturing images with very small object distances, thereby achieving sufficient magnification for the detection of smaller objects. The depth expansion of the objects in the image can considerably exceed the depth of field, and even slight movements of the endoscope can result in major perspective changes of the endoscopic image. In addition, biological objects, like the heart, can not only move, but also dynamically change their shapes and appearances.

Under these conditions, known methods of image enhancement, image stabilization and video enhancement only function inadequately.

It is the object of this invention to overcome these unsolved problems known from prior art and to improve the reproduction of fine, weakly fluorescing object structures in video endoscopy.

According to the invention, the task is solved in such a way that images are recorded as a video simultaneously or sequentially in time in an image channel for reflected light and in an image channel for fluorescent light, and, based on the analysis of the single images of the image channel for reflected light, an enhancement of the respective fluorescent image is made.

For example, the method and its steps as described in the following can be applied,.

In the first image sequence of the image channel of the reflected light, image and/or object features, which can also be found in the last captured single image of the at least two single images, are identified in at least two different single images of the first image sequence. The feature position of the identified image and/or object features is recorded with a precision that corresponds to, or is even more precise than, the size of the fine structure that can be displayed with the endoscopic video system.

All known methods for identifying features or objects can be used to identify image features and record their feature positions. For example, algorithms such as SIFT (scale-invariant feature transform), SURF (speeded-up robust features) or block formation from partial areas of the image are suitable for identifying image features.

The position changes of these identified feature positions are calculated relative to the temporally last single image of the first image sequence recorded with reflected light. The term position change is used in a broader sense here and can, aside from a change in the pixel position, also include features such as rotation angle, magnification or distortion. Based on the identified position changes, a geometric image transformation is formed for each prior single image from the temporally prior single image(s) to the temporally last single image, which geometric image transformation corresponds to the identified position changes. The geometric image transformation formed in this way is used to derive the associated transformation function.

This transformation function that describes this geometric transformation or these geometric transformations from the preceding single image(s) captured in reflected light to the temporally last single image captured in reflected light is applied to the fluorescent image(s) of the second image sequence that were exposed simultaneously or nearly simultaneously, i.e. single images of the image sequence of the image channel for fluorescence. By applying the geometric transformation obtained from the image sequence captured in reflected light to the corresponding fluorescent images of the fluorescence channel, these fluorescent images can be precisely superimposed on temporally preceding fluorescent images (i.e. single images of the fluorescence channel) in order to achieve improved fluorescent images of the fluorescence channel.

The application of each transformation function creates, in each case, a fluorescent image in which fine object structures better match the temporally last fluorescent image than is the case in the fluorescent image that was not transformed geometrically.

This improved fluorescent image or these improved fluorescent images of the second image sequence are used together for calculating an improved fluorescent image of the second image sequence. This improvement can be made by way of addition or averaging of the gray values of the position-improved fluorescent images and the temporally last fluorescent image, for example. Furthermore, aside from spatial filtering, temporal filtering of the position-improved fluorescent images is also possible.

By repeating this procedure described in its steps, the improved fluorescent images result in an improved second image sequence and thus an improved fluorescent video.

Identifying the image and/or object features in the reflection images (also in the single images of the first image sequence) can be simplified by identifying the position change compared to the last single image of the first image sequence indirectly from the position changes between temporally directly consecutive single images of the first image sequence. These single images only differ slightly because of the minimal temporal delay, which makes it considerably easier to find matching features. The geometric transformation to the last single image of the first image sequence can then be formed by performing the geometric transformations between the temporally consecutive single images of the first image sequence one after the other, until the temporally last single image of the first image sequence is reached. Accordingly, the transformation functions describing the transformations can also be performed one after the other and applied to the consecutive fluorescent images.

Alternatively, the method can be applied in steps. For this purpose, a position-corrected averaged single image is created from two temporally consecutive single images of the first image sequence. This averaged single image is geometrically transformed and position-corrected averaged with the temporally last single image of the first image sequence and, if applicable, with additional averaged single images. A weighting according to the number of the averaged number of single images in a weighting step can be performed.

The geometric transformation function mentioned can, in the simplest case, describe an image displacement. Recording the position change of an individual feature position suffices for this simplest possible image improvement. A better compensation of relative movements between the endoscope and the object can be achieved by way of affine transformation. However, it is also possible to use nonlinear geometric transformations. The method according to the invention can then also be used to improve the visibility of fine structures in the fluorescent image for very movable objects, such as the heart muscle or the voice folds.

To increase the robustness of the method according to the invention, several feature positions can be combined by way of averaging or other statistical methods, such as RANSAC (random sample consensus). This will also enable the removal of outliers caused by incorrectly recorded feature positions.

In a particularly advantageous design, feature points of strongly structured objects and/or feature points close to the center of the image are weighted more strongly or used exclusively when determining the geometric transformation function. For example, strongly structured objects can be identified by a higher density of detectable feature points.

In a particularly advantageous design, a compensation of the optical distortion of the endoscope of the endoscopic video system is performed prior to evaluating the feature positions. This can be accomplished by rectifying the respective single image using inverse distortion on the single image prior to identifying the image and/or object features or directly by converting the feature position of the recorded image and/or object features. Rectification considerably improves the statistical analysis of the position changes. This is especially true if linear geometric transformations are used for image enhancement. In this case, the result of improving the fluorescent image can be achieved in that, when applying the geometric transformation to calculate the geometrically improved fluorescent image, the image is again subjected to a distortion that corresponds to the optical distortion of the endoscope. Alternatively, the image channels of fluorescence and reflection can be rectified after recording of the image and prior to detection of image features and identification of the transformation function, and the above-mentioned method can be applied to the rectified images. As a result, the rectified display of both image channels is also easily possible.

According to one embodiment, the single images (reflection images) and the fluorescent images of the first or second image sequence are recorded time-sequentially. To compensate the temporal delay between the reflection image and the associated fluorescent image within the two video image sequences, a temporal interpolation and/or temporal extrapolation of the detected position changes of the identified image features is performed, and the geometric transformation or the geometric transformations are respectively formed from these interpolated and/or extrapolated position changes, or a temporal interpolation and/or extrapolation of the geometric transformations is formed. The application of this embodiment is particularly advantageous if the image is captured by means of a color sensor that records the reflection image and the fluorescent image time-sequentially.

It is particularly advantageous to implement the method in a real-time imaging system for surgical procedures where the surgeon needs fast imaging for motor controlling fine hand movements, which requires a high frame rate of e.g. 60 frames per second. Such high frame rates are associated with a short exposure time for each fluorescent image. Due to the short exposure time, the image noise is particularly disruptive. Implementation can be accomplished on the basis of GPU, ASIC or FPGA, for example.

According to a further embodiment, many feature positions that are spread out as widely as possible across the image are captured in the single images of the first image sequence, and the geometric transformation function is formed by calculating, at positions between the recorded feature positions, the geometric transformation by way of interpolation of the position changes at circumjacent feature positions. At the image borders, this nonlinear geometric transformation can be performed by means of extrapolation of the adjacent feature positions, and the transformation function can be formed accordingly.

According to a further aspect, the method according to the invention is applied to stereo endoscopy. In addition, the feature positions in both stereoscopic half images can be improved in the manner described above for non-stereoscopic images.

In one embodiment, feature positions, which are part of the same object feature, are identified in two stereoscopic half images of the image channel for reflection that were recorded simultaneously or nearly simultaneously, and the stereoscopic geometric transformation from the left to the right stereoscopic single image is then calculated based on these. In this case, the geometric transformation is calculated from the position changes resulting from the perspective difference between the right and the left partial image channel. If there is a sufficiently high density of such feature positions, it is possible to perform an addition or averaging between the left and the right fluorescent image in the image channel of fluorescence. The sensitivity can be doubled by means of a stereoscopic addition. After the addition, the second improved stereoscopic half image can also be formed by an inverse geometric transformation.

In this case, it is particularly advantageous to compensate the lens distortion by way of rectification, to align the magnification between the left and the right image, and to compensate the occurrence of vertical disparity of the stereoscopic images caused by mechanical tolerances. The identified feature points can be used to calculate these corrections.

Thus, using the method according to the invention and according to the further aspect, stereoscopic reflection images and fluorescent images can be presented on the image display device in a stereoscopic central projection that has been adjusted with high accuracy. This results in a very good stereoscopic reproduction, and the fatigue symptoms that are characteristic of poorly adjusted stereoscopy during constant viewing of the stereo image are avoided.

The inventive method according to the first aspect described for non-stereoscopic imaging can be combined with this inventive stereoscopic method according to the further aspect in order to achieve a further enhancement of the visibility of small structures in the fluorescent image.

BRIEF DESCRIPTION OF THE DRAWINGS

The invention will now be explained in more detail using an exemplary embodiment and referencing the figures. The figures show the following:

FIGS. 2A and 2B: Schematic depiction of single images of a first image sequence recorded in visible light and of fluorescent images of a second image sequence recorded under fluorescence-stimulating radiation for illustrating the method according to the invention;

FIGS. 4A and 4B: Application of the transformation functions to the single images of the second image sequence (FIG. 4A) and the superimposing of the transformed single images of the second image sequence into an improved fluorescent image (FIG. 4B);

DETAILED DESCRIPTION

An endoscopic video system 10—herein also video endoscopy system—typically comprises an endoscope 12 and a camera head 14. The endoscope 12 is connected to the camera head 14 by means of a detachable coupling 16.

The camera head 14 has a lens 18 that serves to map the images supplied by the endoscope 12 to an image sensor.

Figure 1:
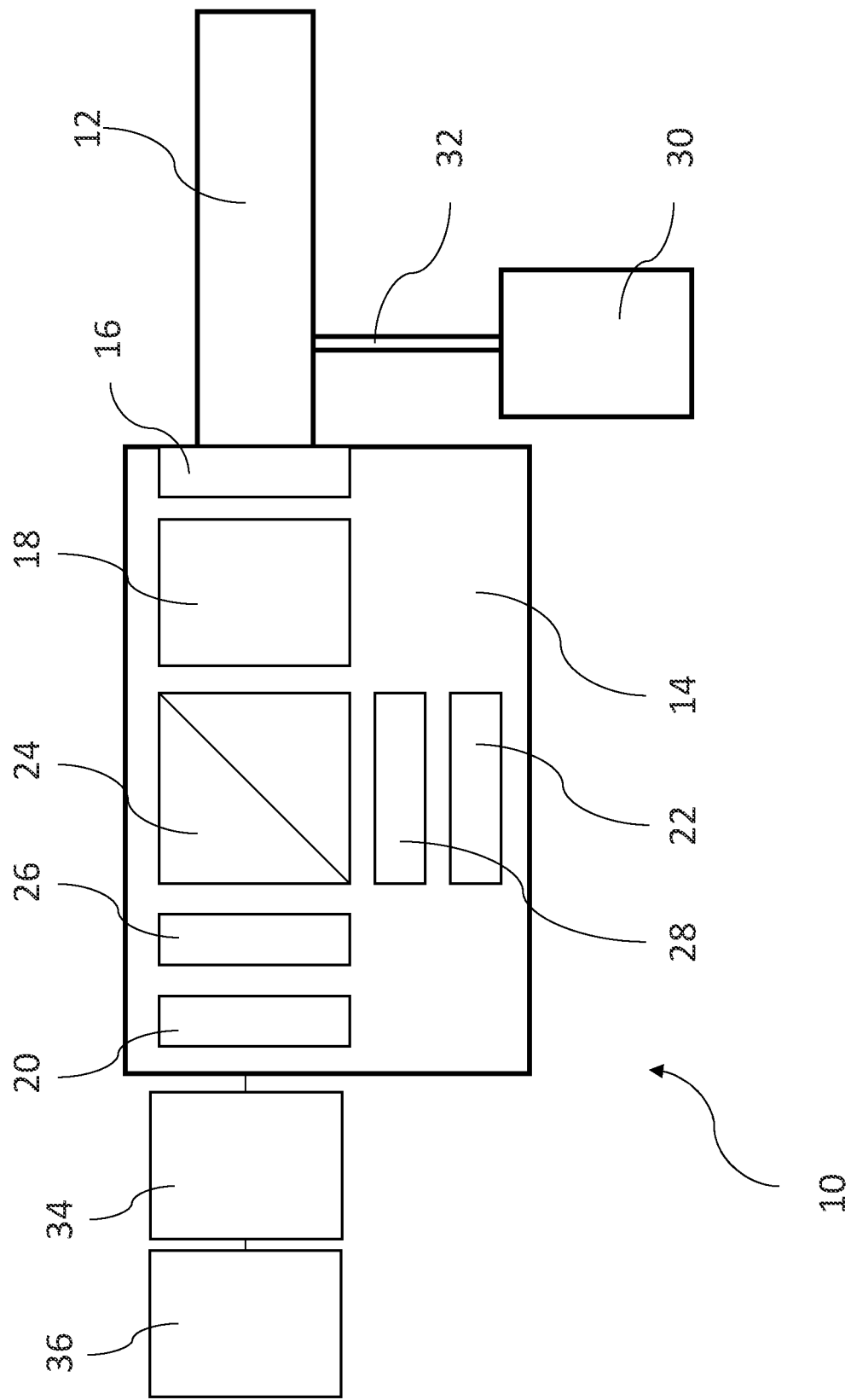
FIG. 1: A video endoscopy system for fluorescence video endoscopy that can be used to simultaneously record video sequences in visible light and video sequences with fluorescent images.

In the example shown in FIG. 1, the camera head 14 has two image sensors, namely an image sensor 20 for visible light and an image sensor 22 for infrared fluorescent images. In order to record single images in visible light with the image sensor 20 as well as fluorescent images with the image sensor 22, a beam splitter 24 is provided that causes the lens 18 to map the optical images on both the image sensor 20 for visible light and on the image sensor 22 for fluorescent images. In order to optically separate the two image channels created this way, a blocking filter 26 for infrared light is provided in front of the image sensor 20 for visible light, which means a blocking filter that blocks infrared light and is transparent for visible light. Accordingly, a blocking filter 28 is provided for the fluorescent images in front of the image sensor 22 that blocks visible light and fluorescence-stimulating light.

In order to illuminate an object to be viewed—which can be located in a body cavity, for example—using the endoscope 12, a light source 30 is provided that feeds light into the endoscope 12 via a light guide 32, so that this light can come out at the distal end of the endoscope 12. The light source 30 provides both visible light and light with a wavelength that is suitable for stimulating fluorescence.

During operation, two image sequences are preferably recorded simultaneously by the two image sensors 20 and 22. The image sensor 20 for visible light records a first image sequence that is comprised of single images, and the image sensor 22 for fluorescent images records a second image sequence that is comprised of fluorescent images. In this case, each single image recorded with the image sensor 20 is associated with a fluorescent image simultaneously recorded with the image sensor 22.

The signals representing the image sequences are supplied to an image processing device 34 that processes the single and fluorescent images as described in the following. The enhanced images of the image sequences generated by the image processing device 34 can then be displayed on a monitor 36 and, due to the image processing described below, in such a way that single images and fluorescent images can be superimposed so that the fluorescence is visible on the monitor 36. In addition, the fluorescent glow can be electronically colored, for example, and added to the color image recorded in reflected light.

Figure 3A:
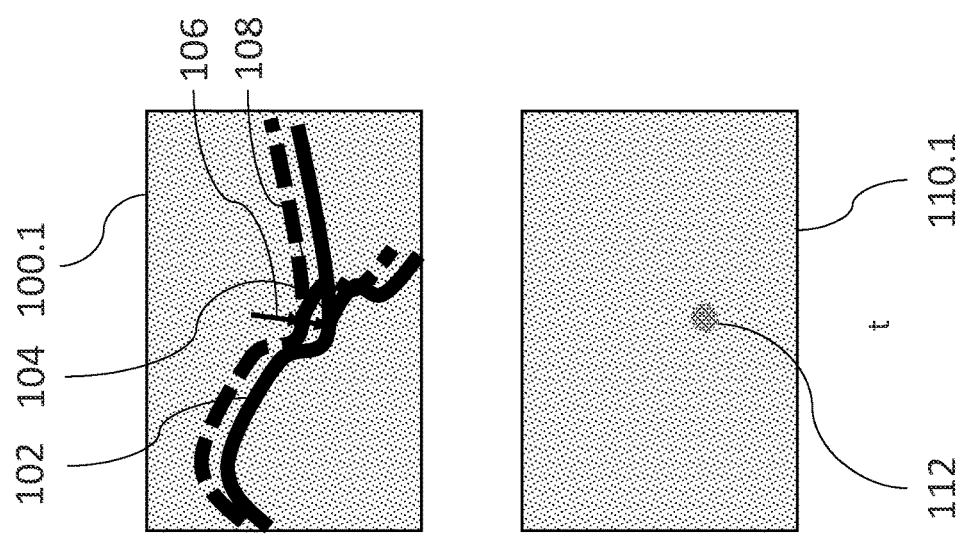
FIGS. 3A and 3B: Schematic depictions of the image changes between consecutive single images of the first and second image sequences analogous to FIGS. 2A and 2B and the associated transformation functions (displacements)

FIG. 2A is an abstract and schematic depiction of three consecutive single images 100 of a first image sequence that were recorded while the object was illuminated with visible light. What is shown is a current single image 100.1 at time t as well as a preceding single image 100.2 at time t-1, as well as a further preceding single image 100.3 at time t-2. As can be seen in FIG. 3A, the single images 100.1, 100.2 and 100.3 differ at the various points in time in that the object 102 shown in the single images 100 is displaced. Using easily identifiable object features (e.g. the structural branching 104), the displacement 106 or 108 by which the two consecutive single images 100 differ can be determined. The displacement 106 or 108 identified this way results in a transformation function that can be used to precisely map a single image 100 at one point in time to a single image 100 at a different (earlier or later) point in time.

FIG. 2B shows three fluorescent images 110 in the second image sequence that were captured while being irradiated with fluorescence-stimulating radiation. The fluorescence 112 only occurs locally and is only faintly visible in a single image. An improved—in particular improved with regard to the signal-to-noise ratio—fluorescent image could be created by superimposing several fluorescent images 110 (which is also roughly equivalent to a longer exposure time). However, the problem is that the fluorescing object 112 is not always located at the same image location in the consecutive fluorescent images of a second image sequence; see FIG. 9.

It is therefore intended to first transform consecutive fluorescent images 110 of the second image sequence so that they can subsequently be superimposed. This is shown schematically in FIGS. 3A, 3B, 4A and 4B. The transformation functions required for transforming the fluorescent images are obtained from the consecutive single images 100 of the first image sequence, for example using procedures known per se, such as SIFT or SURF. FIG. 3A shows how a characteristic object feature 104 can be identified in each single image of the first image sequence. This way, a displacement vector 106 or 108 for a linear displacement can be determined for each transition from one single image 100 to the next single image 100 as a simple transformation function. The displacement vectors that define the transformation function are indicated as arrows in FIG. 3A.

Figure 3B:
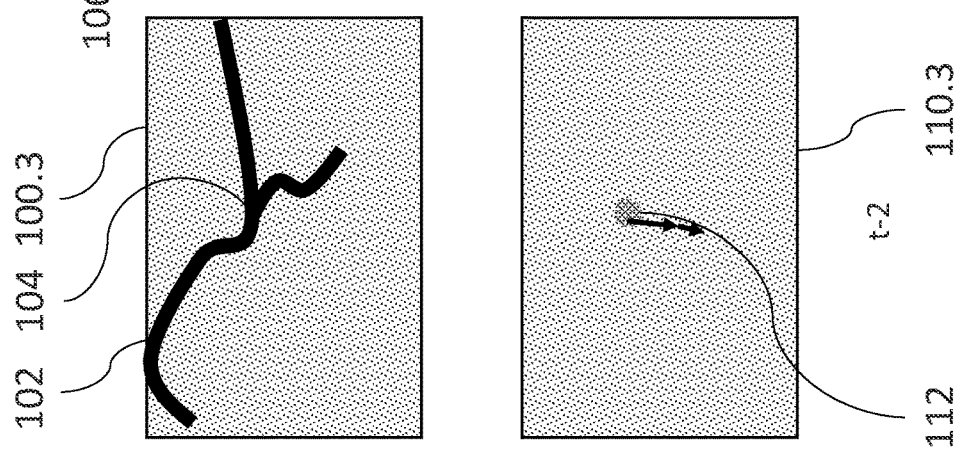

FIG. 3B shows that the same displacements 106 and 108 also apply to the corresponding fluorescent images 110.

Therefore, fluorescent images 110.2 and 110.3 at times t-1 and t-2 that precede a current fluorescent image 110.1 at time t can be transformed in such a way that their image features are position-enhanced and at least approximately congruent as a result; see FIG. 4A. The transformed fluorescent images 110.2' and 110.3' can then be superimposed with the respectively current fluorescent image 110.1 to achieve an enhanced current fluorescent image 114 with improved signal-to-noise ratio; see FIG. 4B.

Figure 5:
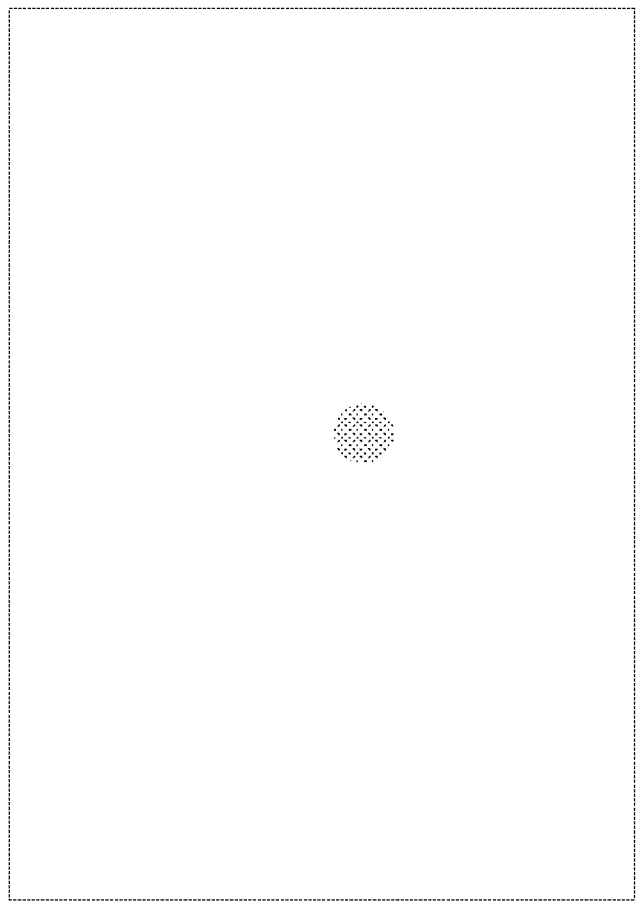
FIG. 5: A schematic depiction of a single fluorescent image with a small structure that has a weak glow in the fluorescent light.

FIG. 5 shows a schematic depiction of a single fluorescent image 110 with a small structure 112 that has a weak glow in the fluorescent light with ideal imaging without image noise.

Figure 6:
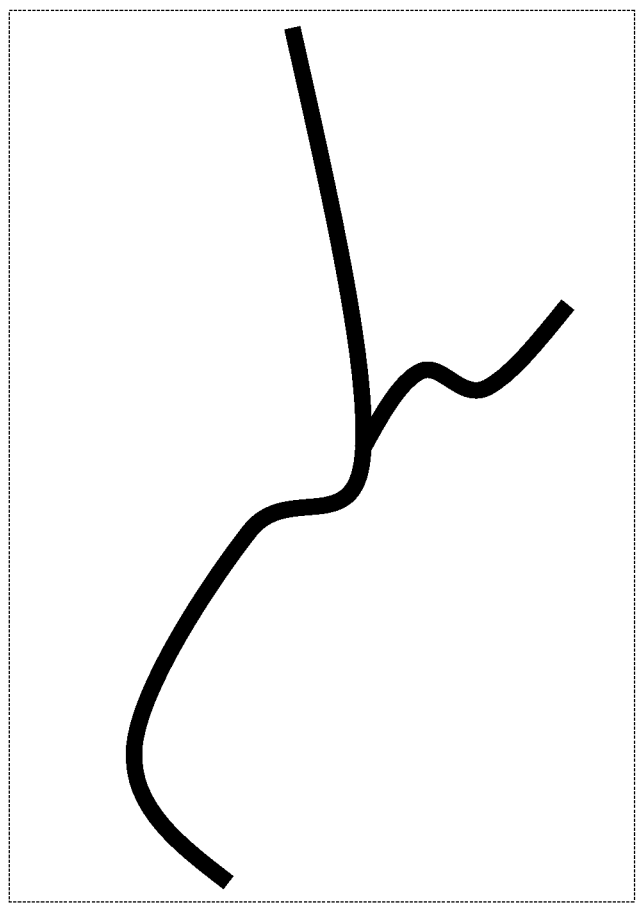
FIG. 6: A schematic depiction of a single image of the first image sequence with a feature in the reflected light.
Figure 7:
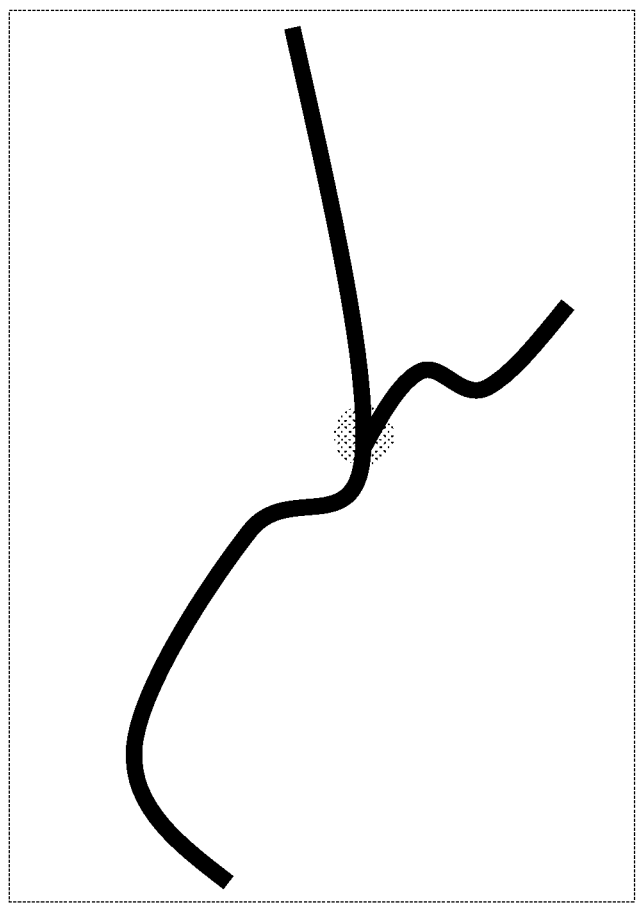
FIG. 7: A schematic depiction of the superimposing of the reflecting structure from FIG. 5 and the fluorescing structures.

FIG. 6 shows a schematic depiction of a single image 100 of the first image sequence with a feature 102 in reflected light with ideal imaging without image noise FIG. 7 shows a schematic depiction of the superimposing of the reflecting structure 102 from FIG. 5 and fluorescing structures 112 with ideal imaging without image noise.

Figure 8:
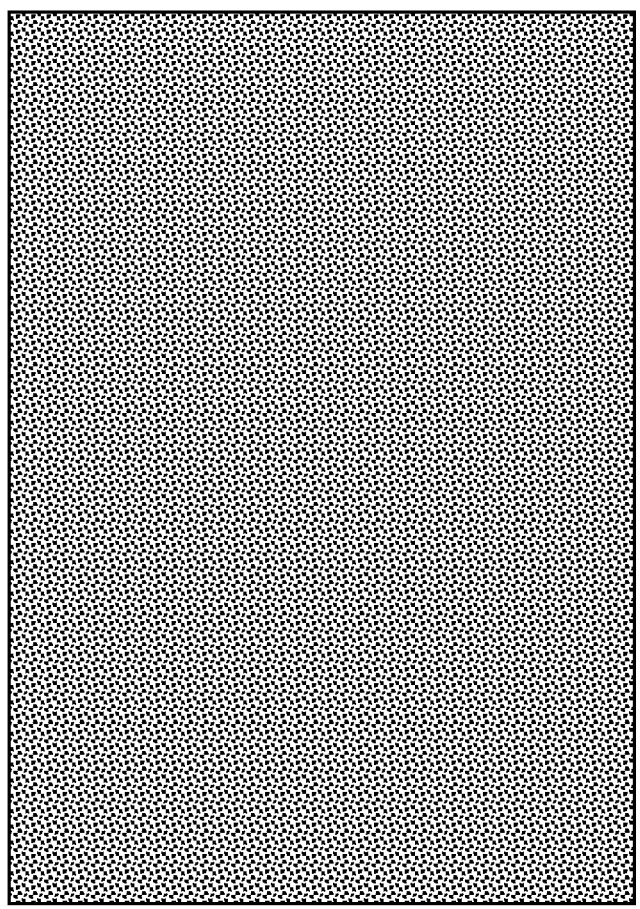
FIG. 8: A schematic depiction of a single fluorescent image from FIG. 5 as it appears on an image sensor.

FIG. 8 shows a schematic depiction of a single fluorescent image 110, like in FIG. 5, as it is recorded by an image sensor. The fluorescing structure 112 is not visible because of the image noise of the image sensor.

Figure 9:
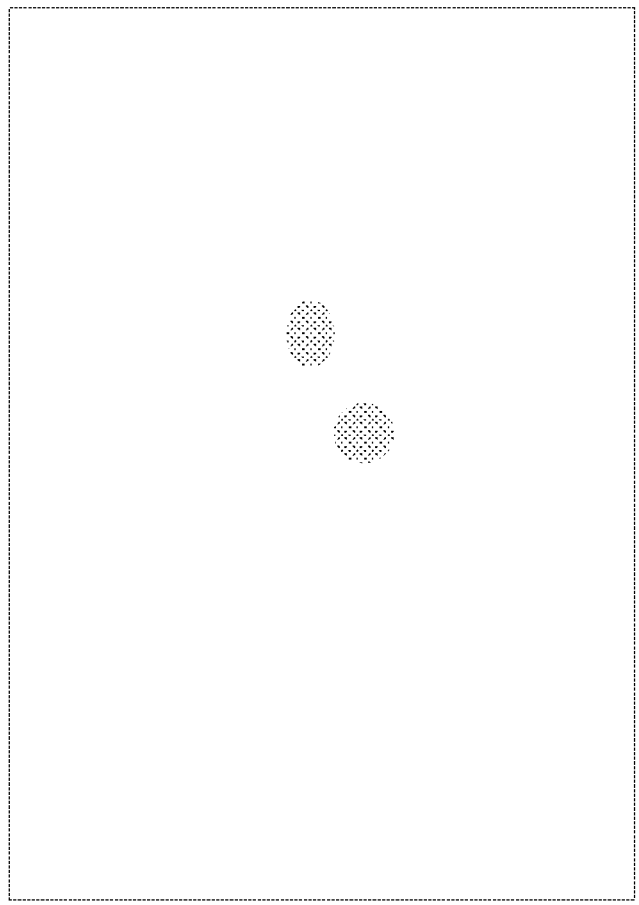
FIG. 9: A schematic depiction of an addition of two superimposed fluorescent images with ideal imaging without image noise.

FIG. 9 shows a schematic depiction of an addition of two superimposed fluorescent images with ideal imaging without image noise. The fluorescing structure is shown twice, i.e. the simple addition of two fluorescent images results in image artifacts instead of the desired amplification of the weak fluorescence.

Figure 10:
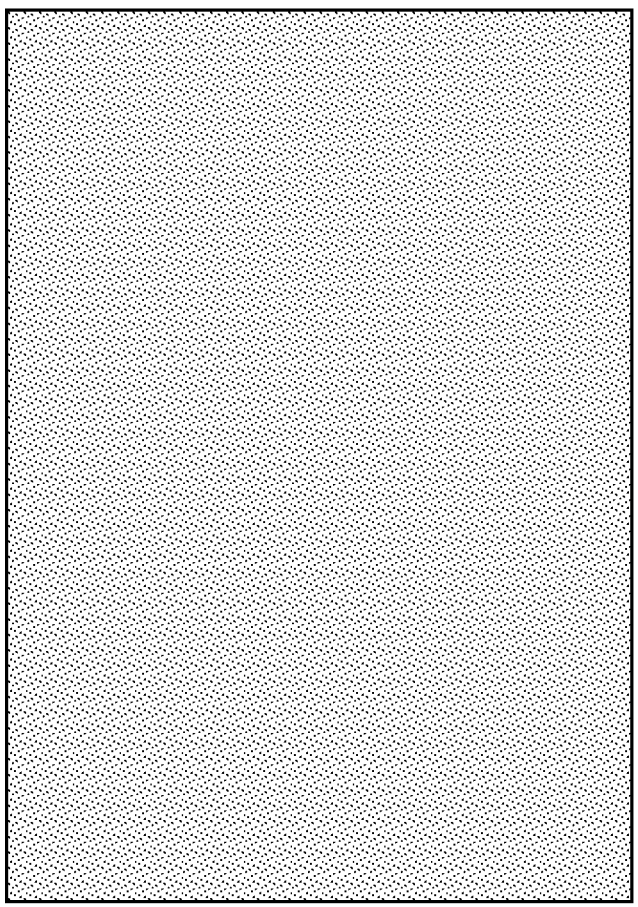
FIG. 10: A schematic depiction of an addition of two superimposed fluorescent images as they are captured by a sensor with image noise.

FIG. 10 shows a schematic depiction of an addition of two superimposed fluorescent images as they are recorded by a sensor with image noise. The noise of the image is reduced. However, the fluorescing structure is still not visible because of the artifacts described in connection with FIG. 9.

Figure 11:
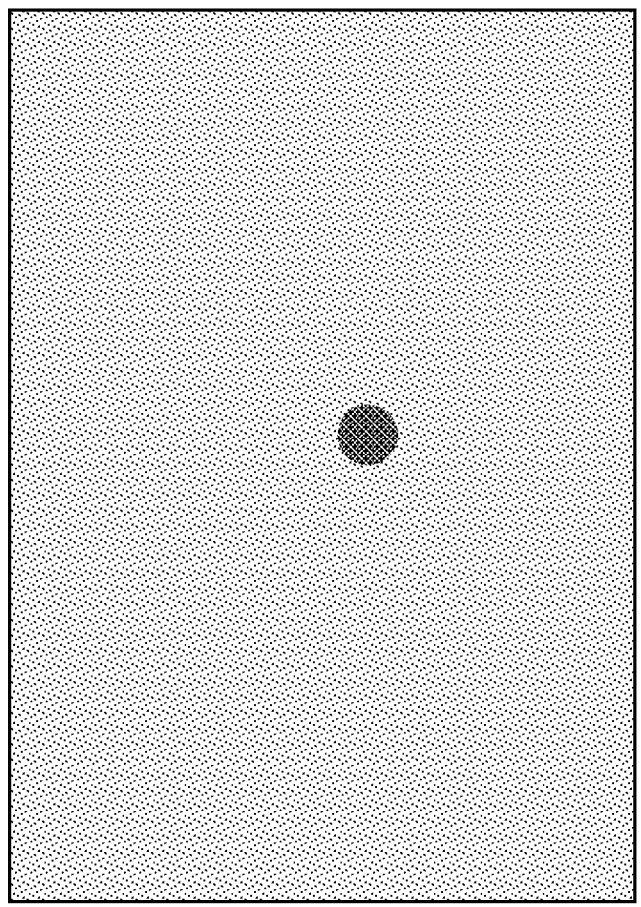
FIG. 11: A schematic depiction of a positionally correct addition performed with the method according to the invention of the two superimposed fluorescent images.

FIG. 11 shows a schematic depiction of a positionally correct addition performed with the method according to the invention of two superimposed fluorescent images. The noise of the image is reduced, and the fluorescing structure is visible.

Figure 12:
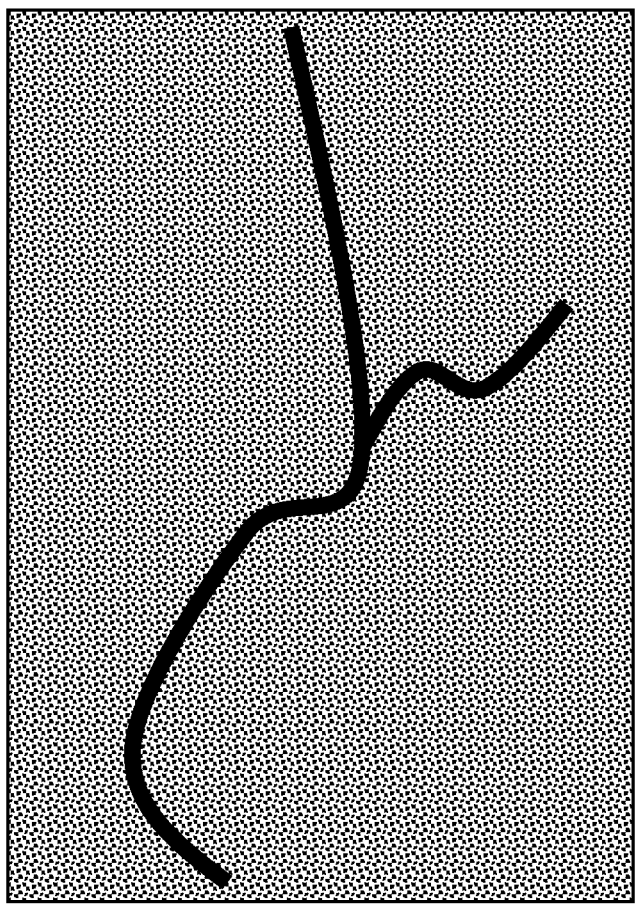
FIG. 12: A schematic depiction of the superimposing of a single image of the first image sequence, that shows reflecting structures, with a single fluorescent image, that shows fluorescing structures, under the influence of the image noise of the sensor.

FIG. 12 shows a schematic depiction of the superimposing of a single image of the first image sequence, that shows reflecting structures, with a single fluorescent image, that shows fluorescing structures, under the influence of the image noise of the sensor. The fluorescing structure is not visible because of the image noise.

Figure 13:
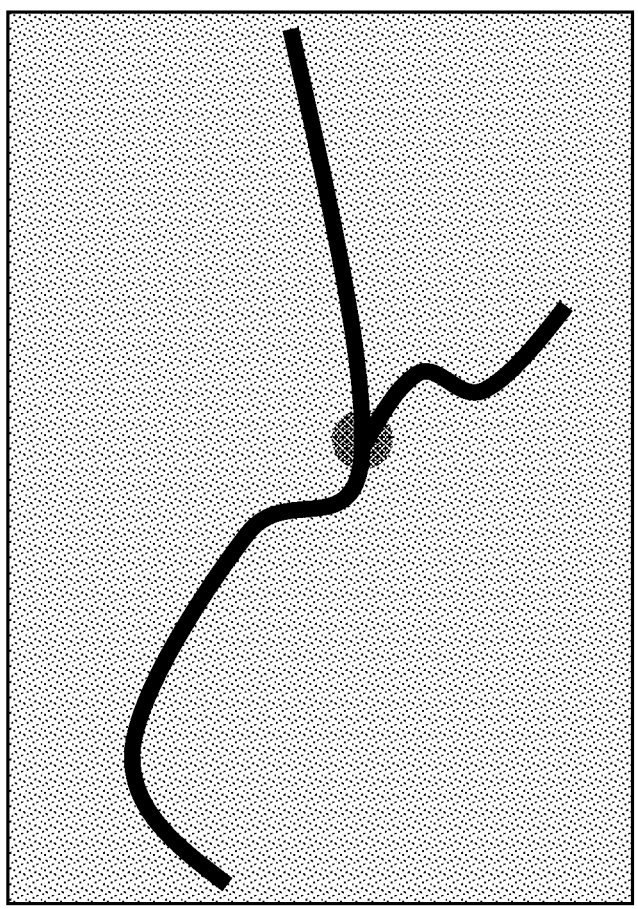
FIG. 13: Image superimposing according to the invention of the reflecting and fluorescing structures, which decreases the image noise and makes the fluorescing structure visible.

FIG. 13 shows an image superimposing of the reflecting and fluorescing structures performed with the invention. The image noise is reduced, and the fluorescing structure is visible.

Figure 14:
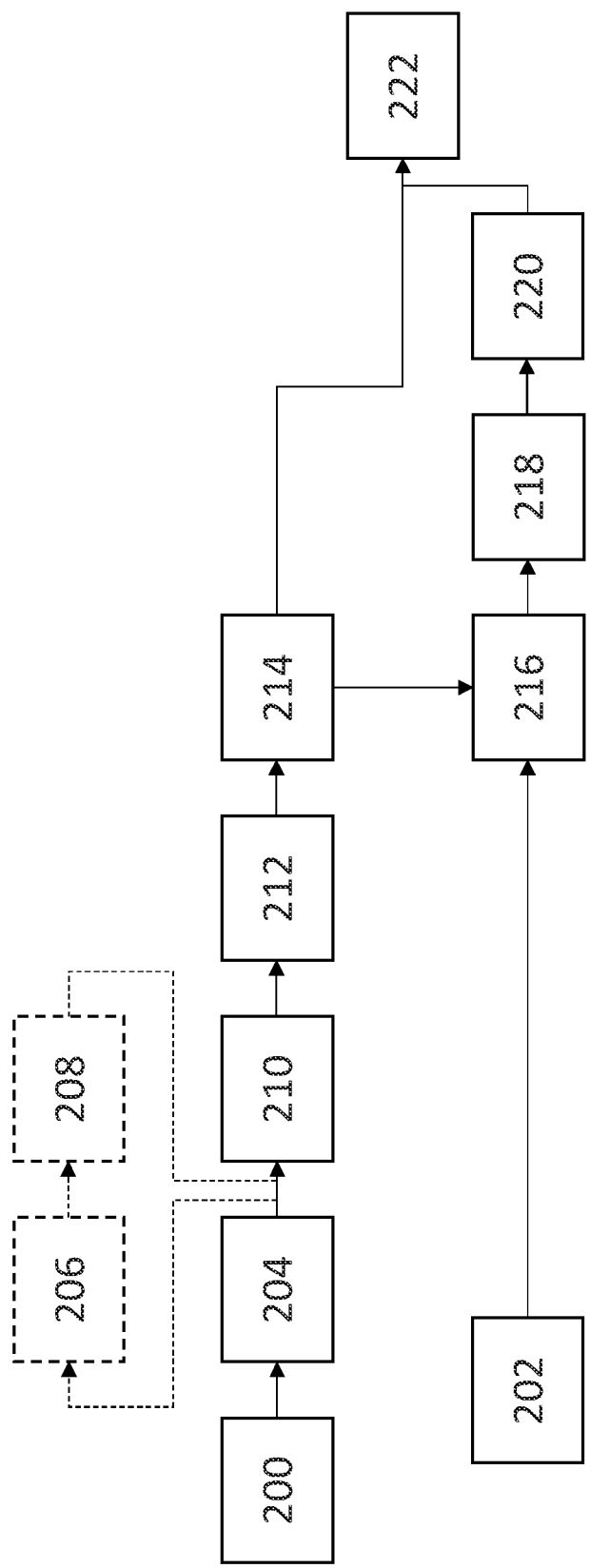
FIG. 14: A schematic depiction of the process of a method according to the invention.

The process of a method according to the invention is as follows (see FIG. 14):

Initially, images of a first image sequence are captured (200), and images of a second image sequence (202) are captured simultaneously or alternately. The images of the first image sequence are single images (reflection images) generated by the light that is reflected by an endoscopically viewed object. The images of the second image sequence are fluorescent images that show fluorescence when an object is irradiated with fluorescence-stimulating radiation.

Subsequently, object or image features are detected (204) in the images of the first image sequence, and the feature positions of the detected object or image features are recorded (206).

The detection of image and/or object features can optionally comprise a rectification of the single images—i.e. a compensation of the optical distortion of the endoscope (208). In addition, an interpolation of the feature positions (210) of the detected object and image features is preferably performed between the feature positions detected in the single images in order to determine interpolated feature positions for points in time at which fluorescent images are captured.

Position changes are determined based on the feature positions recorded in different single images of the first image sequence of a respective detected object or image feature (212). The determined position changes are then used to form geometric transformations (transformation functions) that correspond to the position changes (214).

The transformation functions formed from the single images of the first image sequence are finally applied to fluorescent images of the second image sequence (216) in order to obtain transformed fluorescent images in which fluorescing structures are respectively located at the same image location.

The fluorescent images transformed this way are finally superimposed upon each other (218) in order to obtain an improved fluorescent image.

These steps are carried out for each current fluorescent image to obtain a sequence of improved fluorescent images that can ultimately be displayed (220).

Optionally, each improved fluorescent image can be superimposed on the associated single image of the first image sequence so that a video sequence of superimposed single and fluorescent images is created (22).

LIST OF REFERENCE SIGNS

10 Endoscopic video system
12 Endoscope
14 Camera head
16 Detachable coupling
18 Lens
20 Image sensor for visible light
22 Image sensor for fluorescent images
24 Beam splitter
26 Beam splitter, blocks infrared light
28 Beam splitter, blocks visible light and stimulating light
30 Light source
32 Light guide
34 Image processing device
36 Monitor
100, 100.1, 100.2, 100.3 Single image
102 Object
104 Structural branching
106 Displacement
108 Displacement
110, 110.1, 110.2, 110.3 Fluorescent image
112 Fluorescence, fluorescing object
114 Improved current fluorescent image
200 Capturing a first image sequence in reflected light
202 Capturing a second image sequence in fluorescent light
204 Detection of object or image features
206 Determining the position of object or image features
208 Rectification of the single images
210 Interpolation of feature positions
212 Determination of position changes
214 Formation of transformation functions
216 Application of transformation functions
218 Superimposing of fluorescent images
220 Creating a sequence of fluorescent images
222 Superimposing of single and fluorescent images

What is claimed is:

1. A method for performing a video endoscopy with fluorescent light, with the method comprising the following steps:

Capturing a first image sequence, which is comprised of temporally consecutive single images, each single image is captured using an endoscopic video system in which an object is illuminated and the light reflected by the object is captured as a single image;

Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image, wherein the capturing of the single images and of the fluorescent images of the first or second image sequence occurs either simultaneously, so that each single image can be associated with a simultaneously captured fluorescent image, or a single image or several single images and a fluorescent image or several fluorescent images are captured alternately, so that each single image can be associated with a fluorescent image that was captured before or after the single image with minimal temporal offset;

Determining, by analyzing the single images of the first image sequence, at least one a transformation function between different single images of the first image sequence from position differences of common features in the different single images of the first image sequence;

Applying the transformation function thus determined to the consecutive fluorescent images of the second image sequence that are associated with the single images of the first image sequence to obtain transformed fluorescent images;

Superimposing a current fluorescent image of the second image sequence with at least one or several transformed fluorescent images obtained from the fluorescent images preceding the current fluorescent image in the second image sequence to obtain an improved fluorescent image; and Displaying a respective fluorescent image improved this way, resulting in an improved second image sequence that is comprised of improved fluorescent images.

2. The method according to claim 1, wherein the determination of a transformation function between different single images of the first image sequence comprises the detection of image or object features and the capturing of the feature positions of detected features in single images of the first image sequence.

3. The method according to claim 2, wherein each fluorescent image is associated with exactly one single image of the first image sequence.

4. The method according to claim 3, wherein the fluorescent images and the single images are captured alternately and thus with a minimal temporal delay, and wherein the determination of a transformation function between different single images of the first image sequence comprises an interpolation or extrapolation of captured feature positions in order to determine interpolated or extrapolated feature positions for points in time when a fluorescent image is captured.

5. The method according to claim 1, wherein the determination of a transformation function between different single images of the first image sequence comprises a correction of the optical distortion of the endoscopic video system (rectification).

6. The method according to claim 2, wherein the determination of the image and/or object features in the single images of the first image sequence is simplified by the detection of a position change of image and/or object features compared to the last single image of the first image sequence indirectly from the position changes of detected image and/or object features between temporally directly consecutive single images of the first image sequence.

7. The method according to claim 1, wherein the endoscopic video system comprises a stereo endoscope so that a single image of the first image sequence and a fluorescent image of the second image sequence is respectively composed of a left and a right half image, wherein the feature positions in both stereoscopic half images are improved using the method for performing a video endoscopy with fluorescent light, with the method comprising the following steps:

Capturing a first image sequence, which is comprised of temporally consecutive single images, each single image is captured using an endoscopic video system in which an object is illuminated and the light reflected by the object is captured as a single image;

Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image,
wherein the capturing of the single images and of the fluorescent images of the first or second image sequence occurs either simultaneously, so that each single image can be associated with a simultaneously captured fluorescent image,
or a single image or several single images and a fluorescent image or several fluorescent images are captured alternately, so that each single image can be associated with a fluorescent image that was captured before or after the single image with minimal temporal offset;
Determining a transformation function between different single images of the first image sequence;
Applying the transformation function to the consecutive fluorescent images of the second image sequence that are associated with the single images of the first image sequence to obtain transformed fluorescent images;
Superimposing a current fluorescent image of the second image sequence with at least one or several transformed fluorescent images obtained from the fluorescent images preceding the current fluorescent image in the second image sequence to obtain an improved fluorescent image; and
Displaying a respective fluorescent image improved this way, resulting in an improved second image sequence that is comprised of improved fluorescent images.

8. The method according to claim 7, wherein feature positions, which are part of the same object feature, are identified in two simultaneously or nearly simultaneously captured stereoscopic half images of the first image sequence and used to calculate a stereoscopic geometric transformation from the left to the right stereoscopic single image.

9. The method according to claim 7, wherein an addition or averaging between the left and the right fluorescent half image of the second image sequence is performed.

10. A video endoscopy system with image processing device, wherein the video endoscopy system is configured to capture two image sequences, namely a first image sequence comprised of temporally consecutive single images, with an object being illuminated and the light reflected by the object being captured as a single image, and a second image sequence comprised of temporally consecutive fluorescent images, with the object being irradiated with fluorescence-stimulating radiation and the light emitted by the object being captured as a fluorescent image,
and the image processing device being configured to
associate one or several single images of the first image sequence with one or several fluorescent images of the second image sequence that were captured at least approximately simultaneously;
determine, by analyzing the single images of the first image sequence, transformation functions from the single images of the first image sequence, which transformation functions describe the geometric change of image features between two single images from position differences of common features in the different single images of the first image sequence;
apply the derived transformation functions thus determined to the fluorescent images that correspond to the single images; and
superimpose the fluorescent images transformed this way into an improved fluorescent image.

11. The video endoscopy system according to claim 10, wherein the image processing device has a graphics processing unit (GPU), an application specific integrated circuit (ASIC), or a field programmable gate array (FPGA).

12. The video endoscopy system according to claim 10, which comprises a stereo endoscope.

13. The video endoscopy system according to claim 10, which is configured to perform a method for performing a video endoscopy with fluorescent light, with the method comprising the following steps:
Capturing a first image sequence, which is comprised of temporally consecutive single images, each single image is captured using an endoscopic video system in which an object is illuminated and the light reflected by the object is captured as a single image;
Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image,
wherein the capturing of the single images and of the fluorescent images of the first or second image sequence occurs either simultaneously, so that each single image can be associated with a simultaneously captured fluorescent image,
or a single image or several single images and a fluorescent image or several fluorescent images are captured alternately, so that each single image can be associated with a fluorescent image that was captured before or after the single image with minimal temporal offset;
Determining a transformation function between different single images of the first image sequence;
Applying the transformation function to the consecutive fluorescent images of the second image sequence that are associated with the single images of the first image sequence to obtain transformed fluorescent images;
Superimposing a current fluorescent image of the second image sequence with at least one or several transformed fluorescent images obtained from the fluorescent images preceding the current fluorescent image in the second image sequence to obtain an improved fluorescent image; and
Displaying a respective fluorescent image improved this way, resulting in an improved second image sequence that is comprised of improved fluorescent images.

14. The video endoscopy system according to claim 12, which is configured to perform a method for performing a video endoscopy with fluorescent light, with the method comprising the following steps:
Capturing a first image sequence, which is comprised of temporally consecutive single images, each single image is captured using an endoscopic video system in which an object is illuminated and the light reflected by the object is captured as a single image;
Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image, wherein the capturing of the single images and of the fluorescent images of the first or second image sequence occurs either simultaneously, so that each single image can be associated with a simultaneously captured fluorescent image, or a single image or several single images and a fluorescent image or several fluorescent images are captured alternately, so that each single image can be associated with a fluorescent image that was captured before or after the single image with minimal temporal offset;

Determining a transformation function between different single images of the first image sequence;

Applying the transformation function to the consecutive fluorescent images of the second image sequence that are associated with the single images of the first image sequence to obtain transformed fluorescent images;

Superimposing a current fluorescent image of the second image sequence with at least one or several transformed fluorescent images obtained from the fluorescent images preceding the current fluorescent image in the second image sequence to obtain an improved fluorescent image; and Displaying a respective fluorescent image improved this way, resulting in an improved second image sequence that is comprised of improved fluorescent images, wherein the endoscopic video system comprises a stereo endoscope so that a single image of the first image sequence and a fluorescent image of the second image sequence is respectively composed of a left and a right half image, wherein the feature positions in both stereoscopic half images are improved using a method for performing a video endoscopy with fluorescent light, with the method comprising the following steps:

Capturing a first image sequence, which is comprised of temporally consecutive single images, each single image is captured using an endoscopic video system in which an object is illuminated and the light reflected by the object is captured as a single image;

Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image, wherein the capturing of the single images and of the fluorescent images of the first or second image sequence occurs either simultaneously, so that each single image can be associated with a simultaneously captured fluorescent image, or a single image or several single images and a fluorescent image or several fluorescent images are captured alternately, so that each single image can be associated with a fluorescent image that was captured before or after the single image with minimal temporal offset;

Determining a transformation function between different single images of the first image sequence;

Applying the transformation function to the consecutive fluorescent images of the second image sequence that are associated with the single images of the first image sequence to obtain transformed fluorescent images;

Superimposing a current fluorescent image of the second image sequence with at least one or several transformed fluorescent images obtained from the fluorescent images preceding the current fluorescent image in the second image sequence to obtain an improved fluorescent image; and Displaying a respective fluorescent image improved this way, resulting in an improved second image sequence that is comprised of improved fluorescent images.

15. Using a video endoscopy system according to claim 10 for performing a method for performing a video endoscopy with fluorescent light, with the method comprising the following steps:

Capturing a first image sequence, which is comprised of temporally consecutive single images, each single image is captured using an endoscopic video system in which an object is illuminated and the light reflected by the object is captured as a single image;

Capturing a second image sequence, which is comprised of temporally consecutive fluorescent images, each fluorescent image is captured using the same endoscopic video system in which the object is irradiated with fluorescence-stimulating radiation and the light emitted by the object as a result of the stimulated fluorescence is captured as a fluorescent image, wherein the capturing of the single images and of the fluorescent images of the first or second image sequence occurs either simultaneously, so that each single image can be associated with a simultaneously captured fluorescent image, or a single image or several single images and a fluorescent image or several fluorescent images are captured alternately, so that each single image can be associated with a fluorescent image that was captured before or after the single image with minimal temporal offset;

Determining a transformation function between different single images of the first image sequence;

Applying the transformation function to the consecutive fluorescent images of the second image sequence that are associated with the single images of the first image sequence to obtain transformed fluorescent images;

Superimposing a current fluorescent image of the second image sequence with at least one or several transformed fluorescent images obtained from the fluorescent images preceding the current fluorescent image in the second image sequence to obtain an improved fluorescent image; and Displaying a respective fluorescent image improved this way, resulting in an improved second image sequence that is comprised of improved fluorescent images.

16. The method according to claim 1, wherein each fluorescent image is associated with exactly one single image of the first image sequence.

17. The method according to claim 2, wherein the fluorescent images and the single images are captured alternately and thus with a minimal temporal delay, and wherein the determination of a transformation function between different single images of the first image sequence comprises an interpolation or extrapolation of captured feature positions in order to determine interpolated or extrapolated feature positions for points in time when a fluorescent image is captured.

* * * * *